(12) United States Patent
Kwon et al.

(10) Patent No.: US 12,383,486 B2
(45) Date of Patent: Aug. 12, 2025

(54) HAIR STYLING COMPOSITION AND SPRAY SYSTEM

(71) Applicants: LG CHEM, LTD., Seoul (KR); LG HOUSEHOLD & HEALTH CARE LTD., Seoul (KR)

(72) Inventors: Su Jee Kwon, Daejeon (KR); Hwa Choon Choi, Seoul (KR); Jeong Ae Yoon, Daejeon (KR); In Ho Lee, Seoul (KR); Sung Soo Yoon, Daejeon (KR)

(73) Assignees: LG CHEM, LTD., Seoul (KR); LG HOUSEHOLD & HEALTH CARE LTD., Seoul (KR)

( * ) Notice: Subject to any disclaimer, the term of this patent is extended or adjusted under 35 U.S.C. 154(b) by 1138 days.

(21) Appl. No.: 17/260,770

(22) PCT Filed: Jul. 16, 2019

(86) PCT No.: PCT/KR2019/008752
§ 371 (c)(1),
(2) Date: Jan. 15, 2021

(87) PCT Pub. No.: WO2020/017857
PCT Pub. Date: Jan. 23, 2020

(65) Prior Publication Data
US 2021/0299026 A1    Sep. 30, 2021

(30) Foreign Application Priority Data
Jul. 17, 2018   (KR) .................. 10-2018-0082702

(51) Int. Cl.
*A61K 8/81*   (2006.01)
*A61K 8/04*   (2006.01)
*A61K 8/34*   (2006.01)
*A61Q 5/06*   (2006.01)

(52) U.S. Cl.
CPC ............ *A61K 8/8152* (2013.01); *A61K 8/046* (2013.01); *A61K 8/34* (2013.01); *A61Q 5/06* (2013.01); *A61K 2800/594* (2013.01)

(58) Field of Classification Search
CPC ........ A61K 8/8152; A61K 8/046; A61K 8/34; A61K 2800/594; A61Q 5/06
See application file for complete search history.

(56) References Cited

U.S. PATENT DOCUMENTS

| | | |
|---|---|---|
| 4,196,190 A | 4/1980 | Gehman et al. |
| 5,480,634 A | 1/1996 | Hayama et al. |
| 5,501,851 A | 3/1996 | Mudge et al. |
| 6,214,328 B1 | 4/2001 | Chang et al. |

(Continued)

FOREIGN PATENT DOCUMENTS

| | | |
|---|---|---|
| CN | 102370586 A | 3/2012 |
| CN | 103596549 A | 2/2014 |

(Continued)

*Primary Examiner* — Jianfeng Song
(74) *Attorney, Agent, or Firm* — Bryan Cave Leighton Paisner LLP

(57) ABSTRACT

The present disclosure relates to a hair styling composition. According to one example of the present disclosure, there is provided a hair styling composition having a little beading phenomenon or flaking phenomenon as well as excellent style holding force of the set hair, and capable of providing excellent detergency even after use.

15 Claims, 1 Drawing Sheet

(56) References Cited

U.S. PATENT DOCUMENTS

| | | | |
|---|---|---|---|
| 2007/0197704 A1 | 8/2007 | Walter et al. | |
| 2009/0252689 A1* | 10/2009 | Collin | C08F 2/26 424/47 |
| 2012/0039819 A1 | 2/2012 | Nakatani et al. | |
| 2013/0236397 A1* | 9/2013 | Winter | A61Q 1/00 514/772.6 |

FOREIGN PATENT DOCUMENTS

| | | |
|---|---|---|
| EP | 2106784 A2 | 10/2009 |
| EP | 2433614 A2 | 3/2012 |
| JP | 2004203761 A | 7/2004 |
| JP | 2014516069 A | 7/2014 |
| JP | 2014205650 A | 10/2014 |
| JP | 2017066152 A | 4/2017 |
| KR | 1991-002421 A | 2/1991 |
| KR | 1999-0067122 A | 8/1999 |
| KR | 10-2000-0022807 A | 4/2000 |
| KR | 10-2001-0030417 A | 4/2001 |
| KR | 10-2003-0017652 A | 3/2003 |
| WO | 97/15275 A1 | 5/1997 |

\* cited by examiner

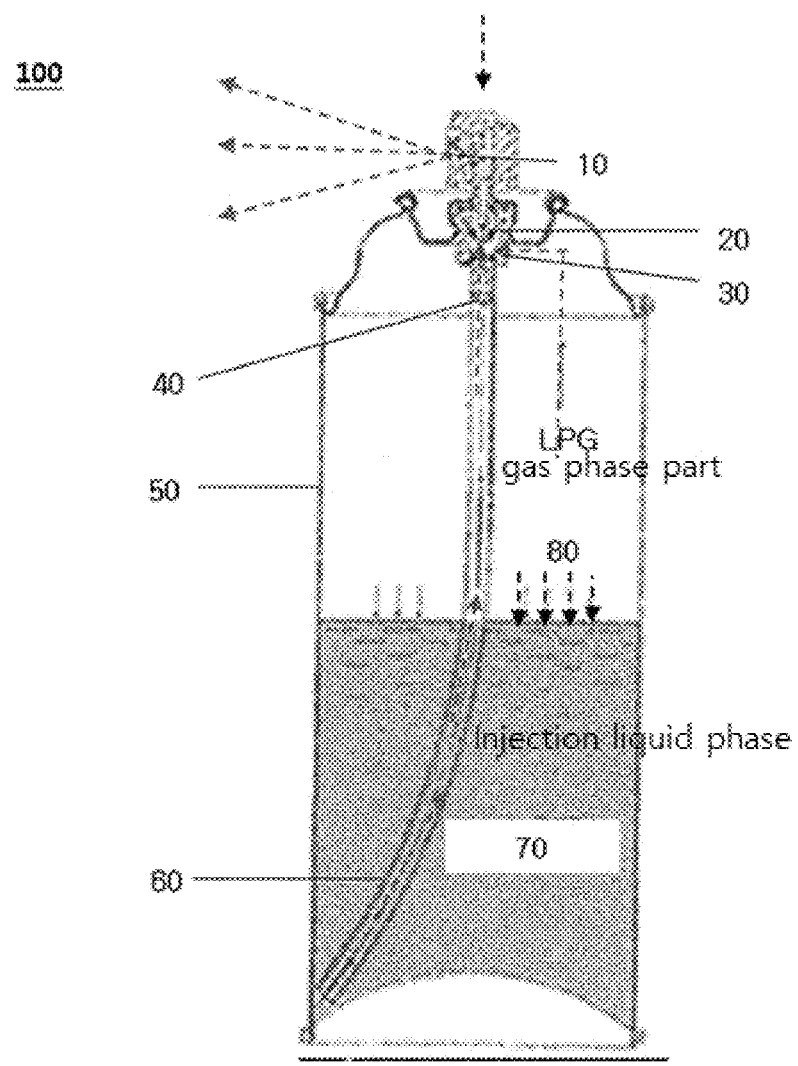

HAIR STYLING COMPOSITION AND SPRAY SYSTEM

CROSS-REFERENCE TO RELATED APPLICATIONS

This application is a National Phase entry pursuant to 35 U.S.C. § 371 of International Application No. PCT/KR2019/008752, filed on Jul. 16, 2019, and claims the benefit of and priority to Korean Patent Application No. 10-2018-0082702, filed on Jul. 17, 2018, all of which are hereby incorporated by reference in their entirety for all purposes as if fully set forth herein.

TECHNICAL FIELD

The present application relates to a hair styling composition and a spray system.

BACKGROUND ART

A variety of products have been released in connection with hair styling. For example, hair sprays, gels, mousses, hair tonics, hair lotions, and the like have been sold. Such products include components (compositions) that contact a user's hair and then maintain the hair designed in a state where the user wants for a predetermined period of time.

For example, in a hair spray, the hair spray composition (aerosol) may comprise a high pressure gas propellant, a solvent and a polymer for hair setting, a plasticizer, a moisturizer, and/or an aroma-providing component, and the like. The composition is stored in a given injection system. For example, when a user presses an injection button formed on a spray container, the composition can be sprayed onto the hair in the form of fine particles, foam or liquid with carrying the gas by the high pressure gas propellant (e.g.: LPG), where the user can design (or set) the hair sprayed with the composition in a desired shape. After the composition is sprayed, the polymer for hair setting in makeups of the composition is a makeup that provides the hair portion set by the user with hair setting holding force (or retention force) for a predetermined time. More specifically, when the solvent (for example, a liquefied gas such as ethanol or LPG) is evaporated after the spray composition is sprayed onto the hair, the polymer for hair setting forms a film on the hair surface, where the hair can be fixed in a state set by the hardness of the film.

As the polymer for hair setting that performs the above action, a polymer soluble in water or alcohol is used. For example, polyvinylpyrrolidone, a vinylpyrrolidone/vinyl acetate copolymer, a vinyl acetate/crotonic acid copolymer or an acrylic resin, and the like are widely used as the polymer for hair setting. After the polymer is sprayed onto the hair, it easily provides a fixing effect for the hair by polymer-specific hardness, but it has a disadvantage of looking excessively hard or being rough and sticky due to its properties to be used together with various additives. That is, it does not provide good beautiful sensation or tactile sensation. Such a polymer has lowered flexibility, and thus when the polymer is subjected to combing after injection or when external force is applied to the fixed hair, the white powder is observed while the coated polymer film is broken (hereinafter, referred to as flaking).

On the other hand, recently, a method of using a silicone-grafted organic main chain polymer in a hair styling product has been introduced. For example, Korean Patent Laid-Open Publication Nos. 10-1999-0067122, 10-2001-0030417 and 10-1991-002421 propose a technique for providing the hair styling holding force and the improved hair touch using a silicone-grafted polymer. However, these compositions are usually sprayed onto the hair while the particles, which are sprayed from a container, form foams, so that it looks like particles such as white snowflakes or white beads are sprayed on black hair (hereinafter, referred to as beading).

DISCLOSURE

Technical Problem

It is one object of the present application to provide a hair styling composition capable of improving a flaking phenomenon and a beading phenomenon.

It is another object of the present application to provide a hair styling composition having excellent beautiful sensation and tactile sensation.

It is another object of the present application to provide a hair styling composition having excellent cleansing properties.

It is another object of the present application to provide a hair styling composition for hair spray.

The above objects and other objects of the present application can be all solved by the present application, which is described in detail below.

Technical Solution

In one example of the present application, the present application relates to a hair styling composition used for contacting hair through an injection, spray or pumping system and fixing the hair in a predetermined shape. The composition provides excellent beautiful sensation and tactile sensation, improves the beading or flaking phenomenon and provides excellent cleaning properties after use, while maintaining the setting state formed by a user for a long time.

The composition comprises a polymer and a solvent.

Specifically, the composition comprises a polymer having a unit represented by the following formula 1. Other chains may be connected to both ends of the following formula 1. The polymer having the following constitution can provide a hair part set by a user with hair setting holding force for a predetermined time, and contributes to providing excellent solubility to a solvent, uniform coating properties to the hair, and excellent cleaning properties upon cleaning the hair after use.

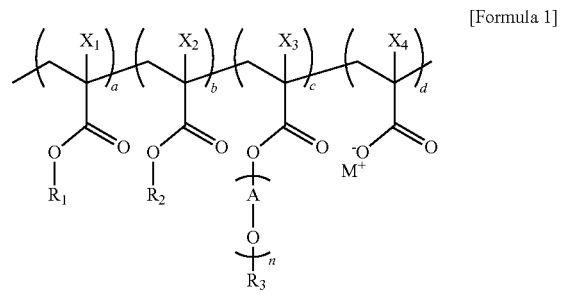

[Formula 1]

In Formula 1 above, $X_1$, $X_2$, $X_3$, and $X_4$ are each independently hydrogen or an alkyl group, $R_1$ and $R_2$ are each an alkyl group having the same or different carbon atoms, A is a divalent hydrocarbon (e.g.: an alkylene group or an alkylidene group), n is an integer between 1 and 50, $R_3$ is hydrogen or an alkyl group, $M^+$ is selected from the group consisting of $Na^+$, $K^+$, imidazolium, ammonium, pyridinium, triazolium, and phosphonium, and a, b, c and d are an average degree of polymerization of each polymerized unit, which are greater than 0, and a+b+c has a value between 50 and 1,000.

Unless otherwise specifically defined in the present application, the alkyl group may mean an alkyl group having 1 to 20 carbon atoms. For example, the alkyl group may mean an alkyl group having 1 to 16 carbon atoms, 1 to 12 carbon atoms, 1 to 8 carbon atoms or 1 to 4 carbon atoms. The alkyl group may be linear, branched or cyclic. The alkyl group may be substituted by one or more substituents, or may be in a state of being unsubstituted.

Furthermore, unless otherwise specifically defined in the present application, the alkylene group or alkylidene group may mean an alkylene group or alkylidene group having 1 to 20 carbon atoms, respectively. For example, the alkylene group or alkylidene group may be an alkylene group or alkylidene group having 1 to 16 carbon atoms, 1 to 12 carbon atoms, 1 to 8 carbon atoms, or 1 to 4 carbon atoms. The alkylene group or alkylidene group may be linear, branched or cyclic. The alkylene group or alkylidene group may be substituted by one or more substituents, if necessary.

The polymer is an anionic acrylic polymer. That is, in the polymer having the unit of Formula 1, $M^+$ has a structure which is not attached to the polymer and is movable while adjusting the ionic balance.

When the polymerization degree is satisfied, the units having average degrees of polymerization of a, b and c contribute mainly to the improvement of the beading phenomenon, the improvement of the flaking phenomenon, the improvement of the cleaning property and the improvement of the solubility of the polymer in the solvent, and the unit having an average degree of polymerization of d contributes mainly to imparting the solubility in water thereto upon hair cleansing after using the styling product. When only one of the units having average degrees of polymerization of a, b and c is included, the above-listed improvement effects cannot be displayed in equilibrium.

In one example, $X_1$, $X_2$, $X_3$ and $X_4$ may be each independently hydrogen or an alkyl group having 1 to 6 carbon atoms.

In one example, $R_1$ may be an alkyl group having 1 to 4 carbon atoms, and $R_2$ may be an alkyl group having 5 to 20 carbon atoms. For example, $R_2$ may be an alkyl group having a carbon number in a range of 5 to 20, 7 to 18 or 9 to 16. When the carbon numbers of $R_1$ and $R_2$ each satisfy the above range, a proper hydrophilic/hydrophobic balance can be realized in the polymer without interfering with the cleaning property so as to achieve the object of the present application.

In one example, A may be a divalent hydrocarbon having 1 to 6 carbon atoms. For example, A may be an alkylene group or an alkylidene group. When the carbon number of A exceeds the above range, the hydrophobicity becomes excessively strong, and thus the cleaning property is deteriorated. For example, A may be an ethylene group or a propylene group. In consideration of such an effect, the ethylene group may be preferable.

In one example, $R_3$ may be hydrogen, or $R_3$ may be an alkyl group having 1 to 6 carbon atoms. When $R_3$ is hydrogen or an alkyl group satisfying 1 to 6 carbon atoms, the solubility of the polymer in a solvent and the cleansing property can be suitably ensured.

In another example, $R_3$ may be hydrogen. In another example, $R_3$ may be a short-chain alkyl group having a carbon number of 3 or less, 2 or less, or 1. A specific example of the short-chain alkyl group may include a methyl group. When $R_3$ is hydrogen or a short-chain alkyl group, it may be advantageous to achieve the effect to be obtained according to the use of the polymer.

The method for producing the polymer containing the unit of Formula 1 above is not particularly limited. For example, when the units having the degrees of polymerization of a, b, c and d are referred to as A, B, C and D units, respectively, the polymer can be obtained by copolymerizing monomers (referred to as precursor monomers) capable of providing the units, respectively.

The monomer components providing the A, B, C and D units can be selected so as to satisfy $X_1$ to $X_4$, $R_1$ to $R_3$, A, $M^+$, etc. of Formula 1 as described above. Examples of the monomer components for preparing the polymer for hair setting are as follows.

In one example, as the A and/or B unit precursor monomers, alkyl (meth)acrylates having an alkyl group with 1 to 20 carbon atoms can be used. For example, methyl (meth)acrylate, ethyl (meth)acrylate, propyl (meth)acrylate, butyl (meth)acrylate, pentyl (meth)acrylate, hexyl (meth)acrylate, 2-ethylhexyl (meth)acrylate, heptyl (meth)acrylate, octyl (meth)acrylate, nonyl (meth)acrylate, hexadecyl (meth)acrylate, lauryl (meth)acrylate, palmityl (meth)acrylate or stearyl (meth)acrylate can be used. In addition, two or more of the foregoing can be used together.

In one example, the numbers of the alkyl groups in the A unit precursor monomer and the B unit precursor monomer may be equal to each other.

In one example, the numbers of the alkyl groups in the A unit precursor monomer and the B unit precursor monomer may be different from each other. For example, as the A unit precursor monomer, an alkyl (meth)acrylate having an alkyl group with 1 to 4 carbon atoms may be used, and as the B unit precursor monomer, an alkyl (meth)acrylate having an alkyl group with 5 to 20 carbon atoms may be used. As described above, when the alkyl groups of the monomers used for forming the A unit and the B unit are adjusted to be different from each other, it is possible to impart an appropriate hydrophobic/hydrophilic balance to the polymer, whereby the beading phenomenon and the flaking phenomenon can be improved, while it has excellent cleaning properties.

In one example, the A and/or B unit precursor monomer may be included in an amount of 15 parts by weight or more, or 20 parts by weight or more, based on 100 parts by weight of the total monomer components for forming the polymer. Specifically, 25 parts by weight or more, 30 parts by weight or more, 35 parts by weight or more, 40 parts by weight or more, 45 parts by weight or more, or 50 parts by weight or more may be used. Then, the A and/or B unit precursor monomer may be used in an amount of 85 parts by weight or less, 80 parts by weight or less, 75 parts by weight or less, or 70 parts by weight or less. When it is used in an amount less than the above range, the hydrophilicity of the polymer becomes too strong, and thus, as confirmed in the following example, the beading phenomenon is intensified, while the contact angle with water becomes low. The beading phenomenon is a phenomenon in which hair spray particles sprayed into the air do not spread evenly on the hair surface and are visible while being rounded and agglomerated, and considering that the hydrophobicity of the hair surface is high, it is considered that the beading phenomenon is improved when the hydrophobicity of the polymer is maintained at a proper level. In addition, when it is used in an amount more than the above range, the solubility in water is lowered while the hydrophobicity of the polymer becomes too strong, whereby upon cleaning a product after use, there is a problem that it is not washed well with water.

In one example, the weight ratio of the A unit precursor monomer to the B unit precursor monomer may satisfy a range of 1:10 to 10:1.

In one example, when the carbon number of the alkyl group in the alkyl (meth)acrylate which is the A unit precursor is shorter than the carbon number of the alkyl group in the alkyl (meth)acrylate which is the B unit precursor, the B unit precursor monomer may be used in excess, as the ratio (Wb/Wa) of the weight (Wb) of the B unit precursor monomer to the weight (Wa) of the A unit precursor monomer is in a range of 1 to 4, 1 to 3.5, 1 to 3, 1 to 2.5, or 1 to 2. When the content range is satisfied, the polymer may have a glass transition temperature in a range of about −10 to 70° C., preferably 10 to 50° C. When the A unit precursor monomer is used in excess, the hardness may become too strong because the polymer has a rigid property as the glass transition temperature of the polymer increases. When the content range is satisfied, the coatability to hair is excellent. However, when it exceeds the above range, the polymer becomes excessively hard, so that the flaking is intensified, and when it is lower than the above range, the flexible property of the polymer becomes strong, so that the styling holding force is lowered.

As the C unit precursor monomer, for example, a hydroxyalkyl (meth)acrylate such as 2-hydroxyethyl (meth)acrylate, 2-methoxyethyl (meth)acrylate, 2-(2-hydroxyethoxy)ethyl (meth)acrylate, 2-(2-methoxyethoxy)ethyl (meth)acrylate, 2-(2-ethoxyethoxy)ethyl (meth)acrylate, poly(ethylene glycol) mono(meth)acrylate, poly(ethylene glycol) mono(alkyl) ether (meth)acrylate, and the like may be used. In addition, two or more of the foregoing may be used together. When such a monomer is used, it may be advantageous to maintain a hydrophilic/hydrophobic balance of the polymer while maintaining solubility in a solvent. In view of this effect, it may be preferred to use a hydroxyalkyl (meth)acrylate.

In one example, the C unit precursor monomer may be contained in an amount of 5 parts by weight or more based on 100 parts by weight of the total monomer components for forming the polymer. Specifically, it may be used in an amount of 10 parts by weight or more, or 15 parts by weight or more. Then, the C unit precursor monomer may be used in an amount of 65 parts by weight or less, 60 parts by weight or less, 55 parts by weight or less, 50 parts by weight or less, 45 parts by weight, 40 parts by weight or less, 35 parts by weight or less, 30 parts by weight or less, 25 parts by weight or less or 20 parts by weight or less. When it is used in an amount less than the above range, the solubility in a solvent is not sufficient, so that for example, it is not suitable for an aerosol formulation or the like necessary for a spray-forming composition, and thus a nozzle clogging phenomenon of a hair spray can be intensified, whereby it is difficult to ensure uniform coatability to hair. In addition, when it is used in an amount more than the above range, the contact angle with water is lowered, so that the beading phenomenon on the hair surface can be intensified.

$M^+$ may be one or more selected from $Na^+$, $K^+$, and quaternary ammonium. In one example, a compound providing the $M^+$ through a predetermined process may be used for D unit formation. For example, as the D unit precursor monomer, an acidic monomer having a crosslinkable functional group and a basic compound (e.g., KOH) may be used, where $K^+$ (potassium ion) as the $M^+$ may be generated by their reaction. Without particular limitation, (meth) acrylic acid may be used as the acidic monomer, and KOH or NaOH may be used as the basic compound for neutralizing it. In addition, a quaternary ammonium salt may be generated when an acidic monomer is neutralized with a compound such as a trialkylamine.

In one example, the D unit precursor monomer may be contained in an amount of 1 part by weight or more based on 100 parts by weight of the total monomer components for forming the polymer. Specifically, it may be used in an amount of 5 parts by weight or more, 10 parts by weight or more, or 15 parts by weight or more. Then, the D unit precursor monomer may be used in an amount of 50 parts by weight or less, 45 parts by weight or less, 40 parts by weight or less, 35 parts by weight or less, 30 parts by weight or less, 25 parts by weight or less, 20 parts by weight or less, 15 parts by weight or less, or 10 parts by weight or less. When it exceeds the above range, the solubility in a solvent or a gas is low, so that there is a problem that it is difficult to produce an aerosol formulation, and when it is less than the above range, sufficient cleaning properties cannot be provided.

In one example, the polymer may have a weight average molecular weight (Mw) in a range of 5,000 to 200,000. For example, the polymer may have a weight average molecular weight of 6,000 or more, 7,000 or more, 8,000 or more, 9,000 or more, 10,000 or more, 11,000 or more, 12,000 or more, 13,000 or more, 14,000 or more, 15,000 or more, 16,000 or more, or 17,000 or more. In addition, for example, the polymer may have a weight average molecular weight of 180,000 or less, 150,000 or less, 120,000 or less, 90,000 or less, 60,000 or less, 30,000 or less, and specifically, may have a weight average molecular weight of 25,000 or less, 24,000 or less, 23,000 or less, 22,000 or less, 21,000 or less, or 20,000 or less. In the present application, the weight average molecular weight may be a converted value of standard polystyrene measured using GPC (gel permeation chromatograph), unless otherwise specified.

In one example, the polymer may have a molecular weight distribution (PDI=Mw/Mn, Mw: weight average molecular weight, Mn: number average molecular weight) in a range of 1.0 to 5.0. For example, the molecular weight distribution may be 1.1 or more, 1.2 or more, 1.3 or more, 1.4 or more, or 1.5 or more. In addition, for example, the molecular weight distribution may be 4.9 or less, 4.8 or less, 4.7 or less, 4.6 or less, 4.5 or less, 4.4 or less, 4.3 or less, 4.2 or less, 4.1 or less, 4.0 or less, 3.9 or less, 3.8 or less, 3.7 or less, 3.6 or less, 3.5 or less, 3.4 or less, 3.3 or less, 3.2 or less, 3.1 or less, or 3.0 or less, and specifically, may be 2.5 or less, 2.4 or less, 2.3 or less, 2.2 or less, 2.1 or less, or 2.0 or less.

In one example, the composition may comprise a polymer (P1) containing the unit of Formula 1 above in a range of 0.1 to 30 parts by weight relative to 100 parts by weight of the entire composition content. For example, the content of the polymer (P1) may be 1 part by weight or more, 2 parts by weight or more, 3 parts by weight or more, 4 parts by weight or more, or 5 parts by weight or more. Alternatively, the content of the polymer within the above range may be 10 parts by weight or more, 15 parts by weight or more, or 20 parts by weight or more.

In one example, the composition may comprise two or more polymers containing the units of Formula 1 above. For example, the composition may comprise a polymer (P11) and a polymer (P12) containing the unit of Formula 1 wherein $R_1$ and the like are different from each other. In this case, the polymer (P1) containing the unit of Formula 1 above may be used in the range of 0.1 to 30 parts by weight relative to 100 parts by weight of the entire composition content.

In another example, the composition may comprise two or more polymers. For example, the composition may comprise a polymer (P1) containing the unit of [Formula 1], as well as may further comprise a heterogeneous polymer (P2) having a different structure. The heterogeneous polymer (P2) having a different structure may mean a polymer not including the unit of [Formula 1]. Alternatively, the composition may further comprise a cationic polymer, an amphoteric (or zwitterionic) polymer, or a nonionic polymer as the polymer (P2), as a concept corresponding to the anionic polymer (P1).

In one example, the composition may further comprise a nonionic polymer such as polyvinylpyrrolidone, a copolymer of polyvinylpyrrolidone/vinyl acetate (PVP/VA copolymer) and a copolymer of polyvinylpyrrolidone/dimethylaminoethyl methacrylate (PVP/dimethylaminoethylmethacrylate copolymer) as the polymer (P2).

In another example, the composition may further comprise an amphoteric polymer (p2) such as a copolymer of methacryloylethyl betaine/methacrylate, and a copolymer of octylacrylamide/acrylate/butylaminoethyl methacrylate.

In another example, it may further comprise two or more polymers of the exemplified polymers (P2).

When the composition comprises both the polymer (P1) and the polymer (P2), the weight ratio (P1:P2) of the polymer (P1) to the polymer (P2) may be in a range of 1:99 to 99:1.

In one example, the polymer (P1) may be used in a content equal to or less than that of the polymer (P2). Specifically, the weight ratio (P1:P2, weight part) between the polymer (P1) and the polymer (P2) may be in the range of 5:95 to 50:50. Specifically, within the above range, the weight ratio of the polymer (P1) may be 10 parts by weight or more, 15 parts by weight or more, 20 parts by weight or more, 25 parts by weight or more, 30 parts by weight or more, 35 parts by weight or more, 40 parts by weight or more, or 45 parts by weight or more.

In another example, the polymer (P1) may be used in an amount equal to or greater than that of the polymer (P2). For example, the weight ratio (P1:P2) between the polymer (P1) and the polymer (P2) may be in the range of 50:50 to 95:5. Specifically, within the above range, the weight ratio of the polymer (P1) may be 55 parts by weight or more, 60 parts by weight or more, 65 parts by weight or more, 70 parts by weight or more, 75 parts by weight or more, 80 parts by weight or more, 85 parts by weight or more, or 90 parts by weight or more.

When the polymer (P1) and the polymer (P2) are used together as above, the total content of the polymers used in the composition may be in a range of 0.1 to 30 parts by weight relative to 100 parts by weight of the total composition content. For example, the total content of the polymer may be 1 part by weight or more, 2 parts by weight or more, 3 parts by weight or more, 4 parts by weight or more, or 5 parts by weight or more. Alternatively, within the above range, the total content of the polymers may be 10 parts by weight or more, 15 parts by weight or more, or 20 parts by weight or more.

In one example, the composition further comprises a solvent. As the solvent, for example, an alcohol such as ethanol or isopropanol may be used. In addition to this, water may be used. For example, a mixture of water and an alcohol may be used as the solvent. When water and an alcohol are mixed and used, the content of water relative to the total solvent component is preferably 10 parts by weight or less.

In one example, the composition may comprise a solvent in a range of 100 to 2,000 parts by weight relative to 100 parts by weight of the polymer components (P1 and/or P2).

In one example, the composition may satisfy a predetermined contact angle. Specifically, the composition may satisfy a contact angle of a water droplet with respect to the coated surface formed from the composition, that is, the film coated with the composition, in a range of 90 to 120°. The contact angle can be measured according to the method described in the following examples. When the contact angle is less than the above range, the coating property of the spray composition to the hair may deteriorate to increase the beading phenomenon, and when the contact angle exceeds the above range, the flaking phenomenon may increase due to an increase in the hard property of the polymer. In addition, as confirmed in the following examples, a polymer having hydrophilic characteristics with too low contact angle is highly soluble in water, and thus it is dissolved in water to produce a product such as a gel product or a lotion product, which has low hardness because it absorbs moisture in the air when used in hair. On the other hand, since a hydrophobic polymer having a high contact angle has low solubility in water, it cannot be used as a gel product or a lotion product, but it is dissolved in ethanol or LPG rather than water to produce a product as a hair spray, which has the highest hardness of hair products, unlike the hydrophilic polymer. Strong hydrophobicity lowers detergency and excessively high hardness easily causes the flaking phenomenon.

In one example, the composition may be an aerosol spray composition that is sprayed in a gas phase. That is, the composition may comprise a high-pressure gas propellant capable of spraying an aerosol. The type of the propellant is not particularly limited, but it may include, for example, one or more of propane, n-butane, isobutane, and dimethyl ether (DME).

In one example, the composition may comprise a propellant in a range of 100 to 1,500 parts by weight relative to 100 parts by weight of the polymer component (P1 and/or P2).

In one example, the composition may further comprise a plasticizer. The kind of the plasticizer is not particularly limited, and for example, known plasticizers such as a silicone compound or 2-amino-2-methyl-1-propanol may be used without limitation.

In one example, the composition may further comprise a humectant. The kind of the humectant is also not particularly limited, and for example, known materials such as propylene glycol may be used without limitation.

In addition, the composition may further comprise additives (pH adjuster, flavor, sunscreen, etc.) capable of providing moisturizing, conditioning and/or flavoring to the hair.

In another example of the present application, the present application relates to a hair spray injection system. The injection system is used to inject the composition, which can be configured such that the composition can be sprayed without clogging the valve.

Specifically, a system configured to inject a composition for hair setting in the form of an aerosol by a high-pressure gas has holes, that is, orifices, of various sizes, so that the composition can be moved and sprayed. Therefore, it is important to appropriately set the size of the orifice according to the composition to be sprayed. That is, depending on the proper design of the orifice, the injection amount of the composition, the size of the particles to be sprayed, the injection shape such as the injection width and the like are determined, and as a result, the function of the entire product for spraying the hair setting agent is influenced.

Referring to FIG. 1 with regards to a description of orifices in an exemplary injection system, when a user presses a button (actuator), the hair spray composition in the container is formed into fine particles (break-up), as it moves inside the valve by means of a propellant and passes through holes such as the body orifice, the vapor tap orifice and the stem orifice, and the composition is sprayed toward the hair in such a way that the finally granulated composition is discharged from the button orifice (actuator orifice). Accordingly, by appropriately designing the orifices so as not to interfere with such a hair composition injection process, the size of the particles to be sprayed or the injection width, and the like should be appropriately made, while the valve is not clogged. Specifically, if the injection amount is too large, the beading phenomenon and the flaking phenomenon may be intensified, and the user's hair may be clumped. In addition, if the size of the sprayed particles is too small, the particles are excessively blown, and thus there is a risk that the user may inhale the hair composition into the nose.

The present application provides an injection system in which the hair setting effect can be sufficiently performed without such a problem.

The system may have a button orifice (actuator orifice), a stem orifice, a body orifice, and a vapor tap orifice.

Furthermore, the system comprises a channel or container, through which the composition can be stored, and a tube.

A predetermined pressure may be formed inside the system.

In one example, the button orifice may have a diameter of 0.3 mm or more, 0.4 mm or more, or 0.5 mm or more. In addition, the upper limit of the diameter of the button orifice may be, for example, 0.7 mm or less, or 0.6 mm or less.

In one example, the system may have one or more stem orifices. For example, the system may have two or more stem orifices.

In one example, the stem orifice may have a diameter of 0.3 mm or more, 0.4 mm or more, or 0.5 mm or more. In addition, the upper limit of the diameter of the stem orifice may be, for example, 0.7 mm or less, or 0.6 mm or less.

In one example, the body orifice may have a diameter of 0.5 mm or more, 0.6 mm or more, or 0.7 mm or more. In addition, the upper limit of the diameter of the body orifice may be, for example, 1 mm or less, 0.9 mm or less, or 0.8 mm or less.

In one example, the vapor tap orifice may have a diameter of, for example, 0.6 mm or less, 0.5 mm or less, 0.4 mm or less, or 0.3 mm or less, and substantially 0 mm. Alternatively, the vapor tap orifice may have no diameter.

When the system is designed to have the number and/or diameter of the orifices as above, the problems described above can be solved and excellent user experiences can be provided.

Advantageous Effects

The present application can solve the prior art problems. For example, according to one example of the present application, a hair styling composition having a little beading phenomenon or flaking phenomenon as well as excellent style holding force of the set hair can be provided. In addition, the composition can provide excellent detergency even after using a hair styling product.

BRIEF DESCRIPTION OF DRAWINGS

FIG. 1 is a schematic view of a spray system.
100: spray system
10: button orifice
20: stem orifice
30: vapor tap orifice
40: body orifice
50: container
60: dip tube
70: mixture of composition and propellant
80: internal pressure

BEST MODE

Hereinafter, the present application will be described in detail by way of examples. However, the scope of protection of the present application is not limited by the following examples.

<Method for Measuring Physical Properties>
*Measurement of Contact Angle

The contact angle was measured using a contact angle measuring instrument (Attension Theta Lite, Biolin Scientific). Specifically, 1 g of each of the compositions compounded as shown in Table 1 was coated on an acrylic plate having a width of 6 cm, a length of 4 cm and a height of 0.3 cm to a uniform thickness (120 μm). Immediately after dropping 4 mg of a water droplet on the coating surface, contact angles of the water droplet with the coating surface was measured at an interval of 1 second for 1 minute, and the average value was obtained. The above calculation was repeated three times while the coating surface positions were set to be different from each other, and the average value was obtained. The contact angle means the angle formed by the tangent of the liquid and the solid surface at the 3 phase contacts of solid (polymer coating surface), liquid (water droplet) and gas (air). The properties of the polymer coating surface were determined according to the contact angle as follows. The results are as shown in Table 2.

less than 50°: hydrophilic polymer with weak hardness, and strong solubility in water
    50° or more to less than 90°: moderate hardness as weak hydrophobicity, and moderate solubility in water
    90° or more to less than 120°: hydrophobicity, high hardness, not large solubility in water
    120° or more: strong hydrophobicity, very high hardness, not suitable for use in hair products

*Beading Evaluation

Two hundred evaluators who actually used hair spray products were allowed to use the hair spray compositions formulated in Examples and Comparative Examples. Sensory tests were conducted. Specifically, the case where there was no injection particle (beading) at the time of injection was evaluated as 10 points, and the case where there were very large injection particles (beading) in the form of beads was evaluated as 1 point, and the average score for each of Examples and Comparative Examples was recorded. The results are as shown in Table 2.

7 to 10 points (good): no beading
4 to 6 points (normal): beading occurs but not so much
1 to 3 points (poor): beading occurs severely

*Flaking Evaluation

Two hundred evaluators who actually used hair spray products were allowed to use the hair spray compositions formulated in Examples and Comparative Examples. Sensory tests were conducted. Specifically, the case where no white powder (flaking) was visibly observed on the hair was evaluated as 10 points, and the case where white powders (flaking) were excessively observed was evaluated as 1 point, and the average score for each of Examples and Comparative Examples was recorded. The results are shown in Table 2.

7 to 10 points (good): no flaking
4 to 6 points (normal): flaking occurs, but not so much
1 to 3 points (poor): flaking occurs severely

EXAMPLES AND COMPARATIVE EXAMPLES

Production of Polymer

Production Example 1

Production of polymer (A1): In a 1 L round bottom flask, 20 g of butyl methacrylate (BMA), 55 g of lauryl methacrylate (LMA), 19 g of 2-hydroxyethyl methacrylate (HEMA), 6 g of methacrylic acid (MAA) and 400 g of ethanol were placed and the flask was sealed, followed by nitrogen bubbling with stirring for 30 minutes. The flask was immersed in an oil bath at 70° C., and 2 g of azobis(isobutyronitrile) (AIBN) was introduced thereto and reacted for 24 hours (in the molecular weight of the produced polymer, Mw was 18,000 and Mw/Mn was 1.73). 3.9 g of KOH was introduced thereto to neutralize the acid groups.

Production Example 2

Production of polymer (A2): In a 1 L round bottom flask, 20 g of butyl methacrylate (BMA), 60 g of lauryl methacrylate (LMA), 14 g of poly(ethylene glycol) monomethyl ether methacrylate (mPEGMA, Mw 500), 6 g of methacrylic acid (MAA) and 400 g of ethanol were placed and the flask was sealed, followed by nitrogen bubbling with stirring for 30 minutes. The flask was immersed in an oil bath at 70° C., and 2 g of azobis(isobutyronitrile) (AIBN) was introduced thereto and reacted for 24 hours (in the molecular weight of the produced polymer, Mw was 19,000 and Mw/Mn was 1.71). 3.9 g of KOH was introduced thereto to neutralize the acid groups.

Production Example 3

Production of polymer (A3): In a 1 L round bottom flask, 20 g of butyl methacrylate (BMA), 55 g of hexadecyl methacrylate (HDMA), 19 g of poly(ethylene glycol) monomethyl ether methacrylate (mPEGMA, Mw 500)), 6 g of methacrylic acid (MAA) and 400 g of ethanol were placed and the flask was sealed, followed by nitrogen bubbling with stirring for 30 minutes. The flask was immersed in an oil bath at 70° C., and 2 g of azobis(isobutyronitrile) (AIBN) was introduced thereto and reacted for 24 hours (in the molecular weight of the produced polymer, Mw was 13,000, and Mw/Mn was 1.68) 3.9 g of KOH was introduced thereto to neutralize the acid groups.

Production Example 4

Polymer (B1): A copolymer under the trade name Amphomer (AkzoNobel), as a zwitterionic polymer and a copolymer of octylacrylamide, acrylate and butylaminoethyl methacrylate, was used.

Production Example 5

Polymer (B2): A copolymer under the trade name Mihapol PAH-50 (Miwon Commercial Co.), as an anionic polymer without b units of the polymer in Examples, unlike Examples, and an AMP-acrylate copolymer, was used.

Production Example 6

Polymer (B3): A copolymer under the trade name Plascize L-301 (GOO Chemical), as a nonionic polymer and a copolymer of hydroxyethyl acrylate, methoxyethyl acrylate and butylacrylate, was used.

Examples and Comparative Examples

Preparation of composition: The respective components were formulated in the ratios described in Table 1 below to prepare a composition for aerosol hair spray. The physical property measurement results for Examples and Comparative Examples are as shown in Table 2.

TABLE 1

| | Example | | | | | Comparative Example | | |
| --- | --- | --- | --- | --- | --- | --- | --- | --- |
| | 1 | 2 | 3 | 4 | 5 | 1 | 2 | 3 |
| Polymer | A1 5 g | A1 2.5 g | A2 2.5 g | A3 2.5 g | A1 4 g | B1 5 g | B2 5 g | B3 5 g |
| | | B1 2.5 g | B1 2.5 g | B1 2.5 g | B1 1 g | | | |
| Solvent | 60 g | 60 g | 60 g | 60 g | 60 g | 60 g | 60 g | 60 g |
| Propellant | 35 g | 35 g | 35 g | 35 g | 35 g | 35 g | 35 g | 35 g |

*Solvent: ethanol

*Propellant: LPG (liquefied petroleum gas)

TABLE 2

|  | Example | | | | | Comparative Example | | |
| --- | --- | --- | --- | --- | --- | --- | --- | --- |
|  | 1 | 2 | 3 | 4 | 5 | 1 | 2 | 3 |
| Beading | good | good | good | good | good | good | normal | Poor |
| Flaking | good | good | good | good | good | poor | poor | good |
| Contact Angle | 112° | 103° | 103° | 108° | 108° | 84° | 66° | 20° |

As shown in Table 2, it can be seen that the compositions configured to comprise predetermined polymers, as in Examples 1 to 5, provide effects that the beading phenomenon is good and the flaking phenomenon is good because the polymers have an appropriate level of hardness. In addition, it can be seen that the compositions of Examples above can have excellent coating properties for hair because the contact angle of the water droplet with respect to the polymer coating satisfies 90 to 120°. However, it can be seen that the compositions of Comparative Examples 1 to 3 cannot improve the beading phenomenon and the flaking phenomenon.

The invention claimed is:

1. A hair styling composition comprising:
a polymer 1 (P1); and
a solvent,
wherein the polymer 1 (P1) contains a unit of Formula 1:

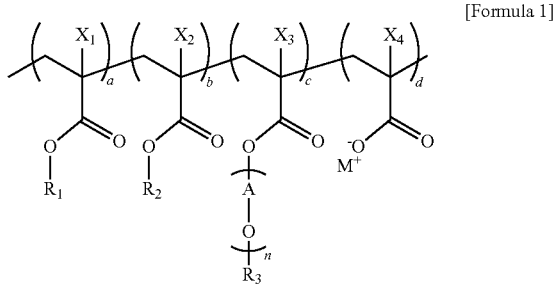

[Formula 1]

wherein,
$X_1$, $X_2$, $X_3$ and $X_4$ are each independently hydrogen or an alkyl group,
$R_1$ is a butyl group,
$R_2$ is an alkyl group having 5 to 20 carbon atoms,
A is an ethylene group,
n is an integer from 1 to 10,
$R_3$ is hydrogen or a methyl group,
$M^+$ is selected from the group consisting of $Na^+$, $K^+$, imidazolium, ammonium, pyridinium, triazolium, and phosphonium, and
a, b, c and d are an average degree of polymerization of each polymerized unit, which are greater than 0, and a+b+c has a value between 50 and 1,000,
wherein a monomer component A' forming the polymerized unit having the average degree of polymerization of a and/or a monomer component B' forming the polymerized unit having the average degree of polymerization of b is included in an amount of 15 parts by weight or more and 85 parts by weight or less based on 100 parts by weight of the total monomer components for forming the polymer, and
wherein a ratio Wb/Wa of a weight Wb of the monomer component B' relative to a weight Wa of the monomer component A' is from 2 to 4.

2. The hair styling composition according to claim 1, wherein $M^+$ is one or more selected from $Na^+$, $K^+$, and quaternary ammonium.

3. The hair styling composition according to claim 1, wherein the polymer 1 (P1) has a weight average molecular weight (Mw) in a range of 5,000 to 200,000 and a molecular weight distribution (PDI) in a range of 1.0 to 5.0.

4. The hair styling composition according to claim 1, wherein the polymer 1 (P1) is contained in a range of 0.1 to 30 parts by weight relative to 100 parts by weight of the total composition content.

5. The hair styling composition according to claim 1, further comprising a polymer 2 (P2) different from the polymer 1 (P1),
wherein the polymer 2 (P2) is selected from one or more nonionic polymers selected from polyvinylpyrrolidone, a copolymer of polyvinylpyrrolidone/vinyl acetate and a copolymer of polyvinylpyrrolidone/dimethylaminoethyl methacrylate; and one or more amphoteric polymers selected from a copolymer of methacryloylethyl betaine/methacrylate and a copolymer of octylacrylamide/acrylate/butylaminoethyl methacrylate.

6. The hair styling composition according to claim 5, wherein the weight ratio of the polymer 1 (P1) to the polymer 2 (P2) is in a range of 1:99 to 99:1.

7. The hair styling composition according to claim 6, wherein the polymers 1 and 2 (P1 and P2) are contained in a range of 0.1 to 30 parts by weight relative to 100 parts by weight of the total composition content.

8. The hair styling composition according to claim 1, wherein the solvent comprises an alcohol or a mixture of an alcohol and water.

9. The hair styling composition according to claim 8, wherein the composition comprises the solvent in a range of 100 to 2,000 parts by weight relative to 100 parts by weight of the polymer 1 (P1).

10. The hair styling composition according to claim 1, wherein the composition is an aerosol spray composition sprayed in a gas phase, and
wherein the composition further comprises one or more materials selected from propane, n-butane, isobutane, and dimethyl ether (DME) as a propellant.

11. The hair styling composition according to claim 10, wherein the composition comprises the propellant in a range of 100 to 1,500 parts by weight relative to 100 parts by weight of the polymer 1 (P1).

12. The hair styling composition according to claim 5, wherein the solvent comprises an alcohol or a mixture of an alcohol and water.

13. The hair styling composition according to claim 12, wherein the composition comprises the solvent in a range of 100 to 2,000 parts by weight relative to 100 parts by weight of the polymers 1 and 2 (P1 and P2).

14. The hair styling composition according to claim 5, wherein the composition is an aerosol spray composition sprayed in a gas phase, and the composition further comprises one or more materials selected from propane, n-butane, isobutane, and dimethyl ether (DME) as a propellant.

15. The hair styling composition according to claim 14, wherein the composition comprises the propellant in a range of 100 to 1,500 parts by weight relative to 100 parts by weight of the polymers 1 and 2 (P1 and P2).

\* \* \* \* \*